United States Patent [19]

Smith et al.

[11] Patent Number: 5,753,218

[45] Date of Patent: May 19, 1998

[54] METHOD FOR TREATING INFLAMMATION

[75] Inventors: Sidney R. Smith, Ridgewood; Satwant K. Narula, West Caldwell, both of N.J.

[73] Assignee: Schering Corporation, Kenilworth, N.J.

[21] Appl. No.: 642,816

[22] Filed: May 3, 1996

[51] Int. Cl.[6] .................................................. A61K 45/05
[52] U.S. Cl. ..................... 424/85.2; 424/85.1; 424/85.5; 514/171; 514/2
[58] Field of Search ............... 514/171, 2; 424/85.2, 424/85.1, 85.5

[56] References Cited

U.S. PATENT DOCUMENTS

| | | | |
|---|---|---|---|
| 5,077,284 | 12/1991 | Loria et al. | 514/171 |
| 5,231,012 | 7/1993 | Mosmann et al. | 435/69.52 |
| 5,342,615 | 8/1994 | Nakai et al. | 514/2 |
| 5,368,854 | 11/1994 | Rennick | 424/85.2 |
| 5,376,368 | 12/1994 | Ulich | 424/85.2 |
| 5,449,515 | 9/1995 | Hamilton et al. | 424/85.2 |
| 5,488,032 | 1/1996 | Dower et al. | 424/85.2 |
| 5,601,815 | 2/1997 | Powtie et al. | 424/85.2 |

FOREIGN PATENT DOCUMENTS

| | | |
|---|---|---|
| WO 91/07186 | 5/1991 | WIPO . |
| WO 93/02693 | 2/1993 | WIPO . |
| WO 97/05895 | 2/1997 | WIPO . |

OTHER PUBLICATIONS

Marchant, et al., 1996, *Clinical and Experimental Immunology* 106 (1):91–96.

Joyce, et al., 1996, *Journal of Interferon and Cytokine Research* 16 (7):511–517.

*Primary Examiner*—James H. Reamer
*Attorney, Agent, or Firm*—Norman C. Dulak; Cynthia L. Foulke

[57] ABSTRACT

A method is provided for treating or preventing inflammatory conditions, in particular septic shock and inflammatory conditions caused by auto-immune diseases, such as inflammatory bowel disease, rheumatoid arthritis, multiple sclerosis, uveitis, and psoriasis. The method comprises administering to a mammal a therapeutically effective amount of IL-10 plus at least one steroid such as betamethasone. Also provided are pharmaceutical compositions and kits comprising IL-10 plus at least one steroid, e.g., betamethasone or its derivatives.

24 Claims, 3 Drawing Sheets

METHOD FOR TREATING INFLAMMATION

FIELD OF THE INVENTION

This invention relates to a method for treating inflammatory conditions or diseases relating to inflammation, including septic shock.

BACKGROUND OF THE INVENTION

One of the mechanisms by which the immune system normally regulates itself includes the production of proteins called cytokines. Cytokines mediate numerous immune/inflammatory responses. Several cytokines, such as tumor necrosis factor alpha (TNF-α), interleukin-1 (IL-1), interferon gamma (IFN-γ), and Interleukin-6 (IL-6), are produced by stimulated monocytes/macrophages and have been implicated in many of the inflammatory, immunological, hematological, and metabolic changes occurring during infection and tissue injury [See, e.g., Hart et al., Proc. Natl. Acad. Sci. 86:3803(1989)].

Septic shock is one example of a disease state characterized by production of inflammatory cytokines. It is an often fatal condition usually resulting from gram-negative bacteremia. Despite the use of potent antibiotics and intensive care, there is still a high mortality rate for sepsis as well as for cases of gram-negative bacteremia which result in septic shock (See, e.g., Ziegler et al., New Eng. J. Med. 324:429 (1991); Bone et al., New Eng. J. Med. 317:653 (1987); and Kreger et al., Am. J. Med 68:344 (1980)). Approximately 100,000–300,000 cases of sepsis-causing gram-negative bacteremia are reported per year, with the resulting deaths estimated at 30,000 to 100,000 (Wolff, New Eng. J. Med. 324:486 (1991)). Sepsis requires prompt treatment, since the patient's condition often deteriorates rapidly. It is a leading cause of morbidity and mortality among hospitalized patients. The symptoms of septic shock include fever or hypothermia, tachycardia, tachypnea, hypotension, peripheral hypoperfusion or systemic toxicity. (Ziegler et aL, supra).

Among treatments currently under investigation for septic shock are the administration of antibodies directed against tumor necrosis factor (TNF-a), Interleukin-1 (IL-1) and lipopolysacchride (LPS). Unfortunately, these treatments have proven disappointing in clinical trials, showing inconsistent or negligible results (See e.g., Gibaldi, Pharmacotherapy (United States) 13:302 (1993) and Colletti et al., Crit. Care Nurs. North Am. 5:345 (1993)). There is thus a need for effective treatment for inflammatory conditions, especially septic shock.

Among other inflammatory conditions treatable or preventable by this invention are those caused by auto-immune diseases which exhibit inflammation as a symptom, such as inflammatory bowel disease, rheumatoid arthritis, multiple sclerosis, uveitis, psoriasis, etc.

SUMMARY OF THE INVENTION

This invention fills the foregoing need by providing a method for treating or preventing inflammatory conditions in a mammal comprising administering an effective amount of a combination of IL-10 and at least one steroid to a mammal in need of such treatment. In particular, this invention provides a method for treating or preventing septic shock, inflammatory bowel disease, rheumatoid arthritis, multiple sclerosis, uveitis, and psoriasis in a mammal comprising administering an effective amount of a combination of IL-10 and at least one steroid to a mammal in need of such treatment. Another aspect of this invention is a pharmaceutical composition comprising a combination of IL-10 and at least one steroid, and a physiologically acceptable carrier. Yet another aspect of this invention is a kit for treating or preventing an inflammatory condition in a mammal comprising in combination an effective amount of IL-10 admixed with a pharmaceutical carrier and an effective amount of a steroid admixed with a pharmaceutically carrier.

DETAILED DESCRIPTION OF THE INVENTION

Figure 1:
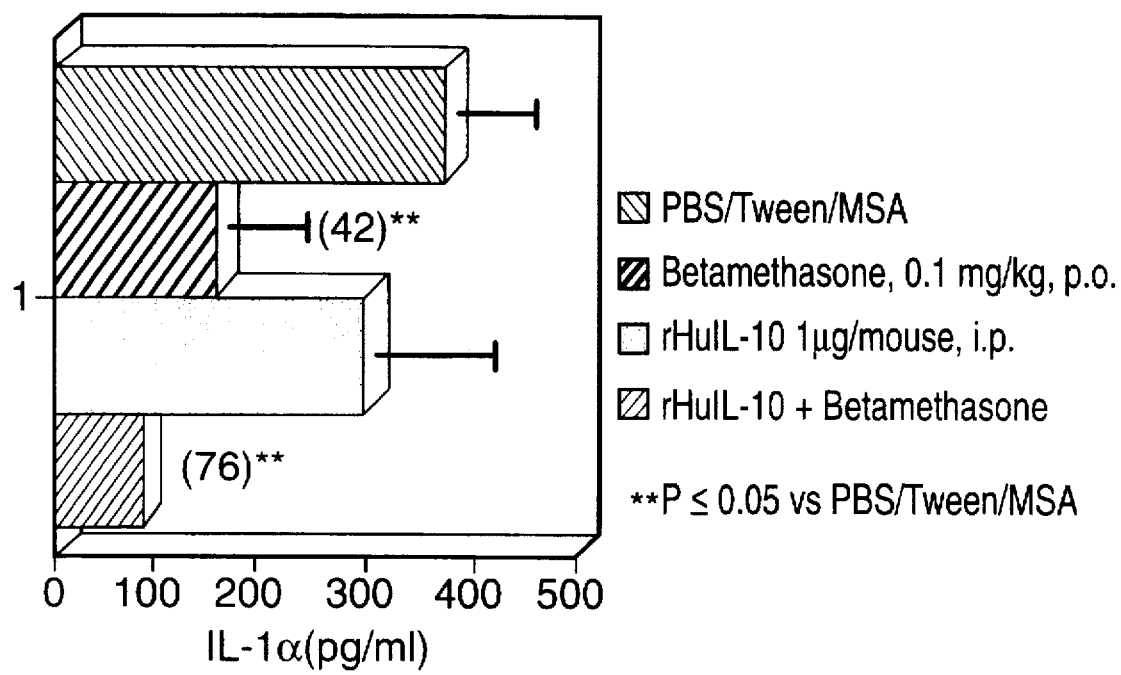
FIG. 1 illustrates the in vivo effect of recombinant IL-10 and/or the steroid betamethasone phosphate on LPS (lipopolysaccharide)-induced serum IL-1 in mice primed with C. parvum. The data marked with double asterisks indicate $P \leq 0.05$ compared to PBS/Tween/MSA.
Figure 2:
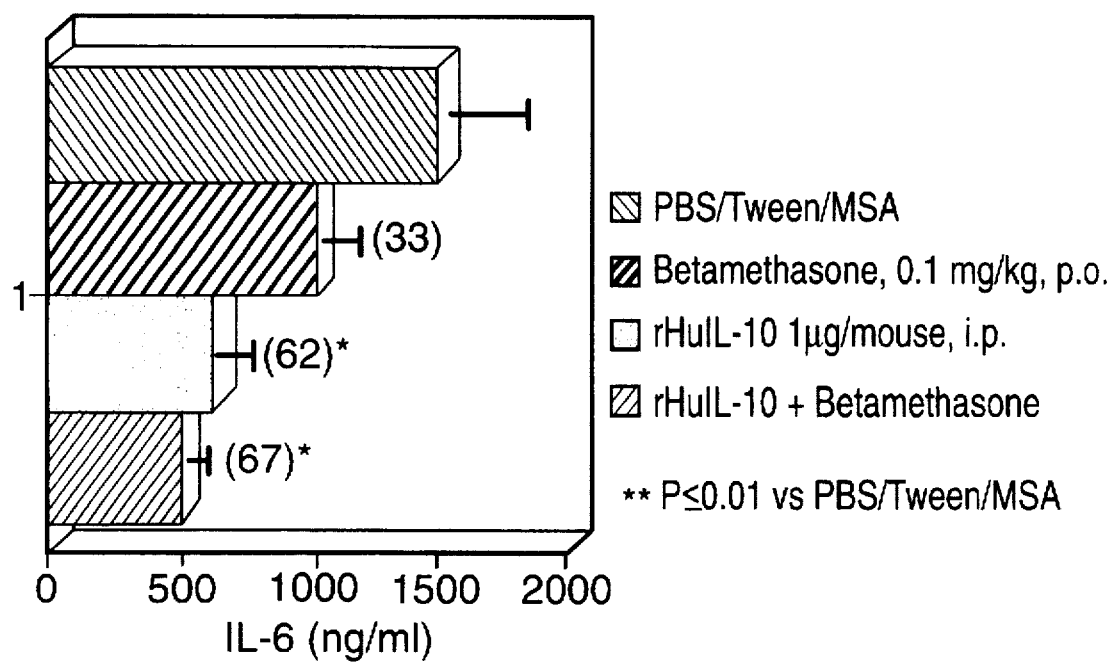
FIG. 2 illustrates the in vivo effect of recombinant IL-10 and/or the steroid betamethasone phosphate on LPS-induced serum IL-6 in mice primed with C. parvum. The data marked with double asterisks indicate $P \leq 0.01$ compared to PBS/Tween/MSA.
Figure 3:
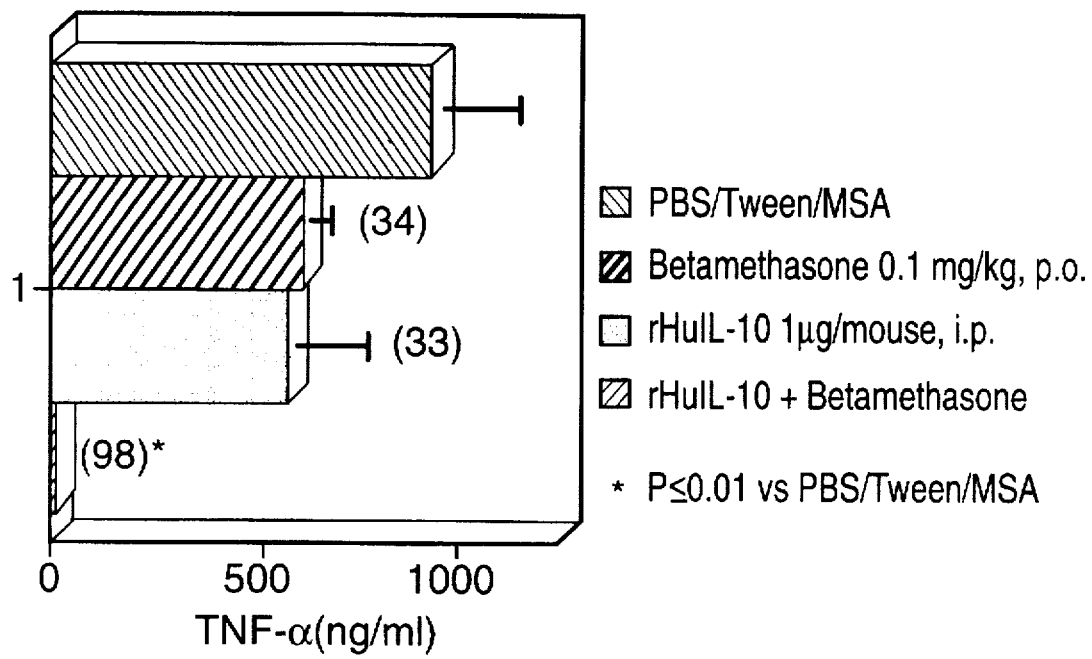
FIG. 3 illustrates the in vivo effect of recombinant IL-10 and/or the steroid betamethasone phosphate on LPS-induced serum TNF-α in mice primed with C. parvum. The data marked with double asterisks indicate $P \leq 0.01$ compared to PBS/Tween/MSA.
Figure 4:
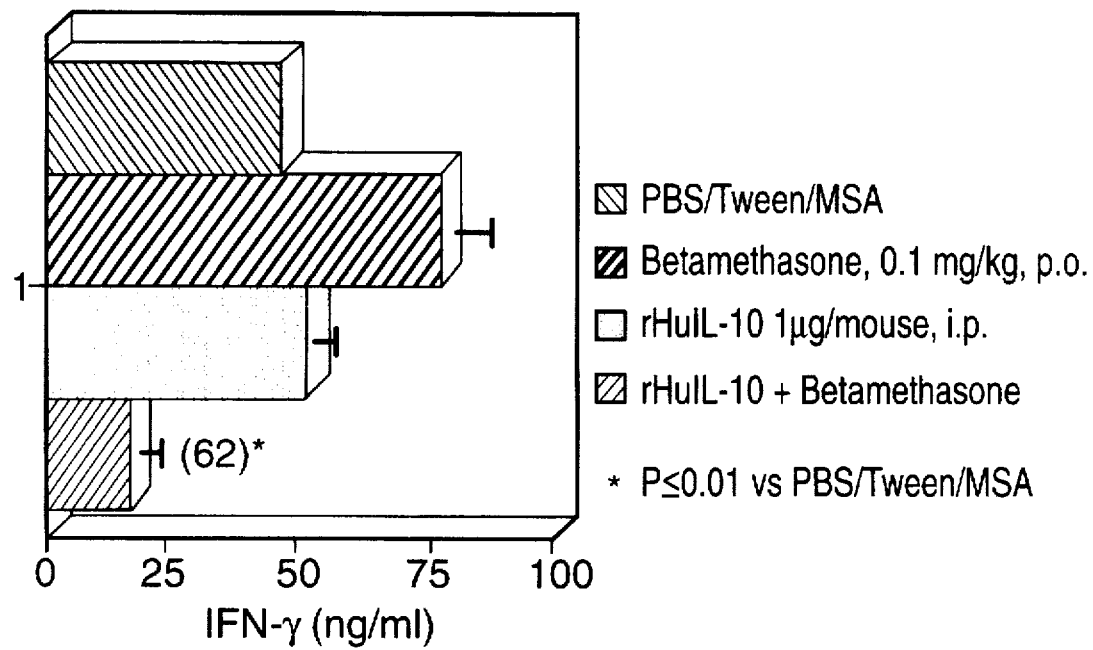
FIG. 4 illustrates the in vivo effect of recombinant IL-10 and/or the steroid betamethasone phosphate on LPS-induced serum IFN-γ in mice primed with C. parvum. The data marked with double asterisks indicate $P \leq 0.01$ compared to PBS/Tween/MSA.

All references cited herein are hereby incorporated in their entirety by reference.

As used herein, "interleukin-10" or "IL-10" is defined as a protein which (a) has an amino acid sequence of mature IL-10 (e.g., lacking a secretory leader sequence) as disclosed in U.S. Pat. No. 5,231,012 and (b) has biological activity that is common to native IL-10. Also included are muteins and other analogs, including the Epstein-Barr Virus protein BCRF1 (viral IL-10), which retain the biological activity of IL-10.

IL-10 suitable for use in the invention can be obtained from culture medium conditioned by activated cells secreting the protein, and purified by standard methods. Additionally, the IL-10, or active fragments thereof, can be chemically synthesized using standard techniques known in the art. See Merrifield, Science 233:341 (1986) and Atherton et al., Solid Phase Peptide Synthesis: A Practical Approach, 1989, I.R.L. Press, Oxford. See also U.S. Pat. No. 5,231,012.

Preferably, the protein or polypeptide is obtained by recombinant techniques using isolated nucleic acid encoding the IL-10 polypeptide. General methods of molecular biology are described, e.g., by Sambrook et al., Molecular Cloning, A Laboratory Manual, Cold Spring Harbor, N.Y., 2d ed., 1989, and by Ausubel et al., (eds.) Current Protocols in Molecular Biology, Green/Woley, New York (1987 and periodic supplements). The appropriate sequences can be obtained using standard techniques from either genomic or cDNA libraries. Polymerase chain reaction (PCR) techniques can be used. See, e.g., *PCR Protocols: A Guide to Methods and Applications*, 1990, Innis et al., (Ed.), Academic Press, New York, N.Y.

Libraries are constructed from nucleic acid extracted from appropriate cells. See, e.g., U.S. Pat. No. 5,231,012, which discloses recombinant methods for making IL-10. Useful gene sequences can be found, e.g., in various sequence databases, e.g., GenBank and BMPL or nucleic acid and PIR and Swiss-Prot for protein, c/o Intelligenetics, Mountain View, Calif., or the Genetics Computer Group, University of Wisconsin Biotechnology Center, Madison, Wis.

Clones comprising sequences that encode human IL-10 have been deposited with the American Type Culture Collection (ATCC), Rockville, Md., under Accession Nos. 68191 and 68192. Identification of other clones harboring the sequences encoding IL-10 is performed by either nucleic acid hybridization or immunological detection of the encoded protein, if an expression vector is used. Oligonucleotide probes based on the deposited sequences disclosed in U.S. Pat. No. 5,231,012 are particularly useful. Oligonucleotide probes sequences can also be prepared from conserved regions of related genes in other species. Alternatively, degenerate probes based on the amino acid sequences of IL-10 can be used.

Standard methods can be used to produce transformed prokaryotic, mammalian, yeast or insect cell lines which express large quantities of the polypeptide. Exemplary *E. coli* strains suitable for both expression and cloning include W3110 (ATCC Bi, 27325), X1776 (ATCC No. 31244), X2282, and RR1 (ATCC Mp/31343). Exemplary mammalian cell lines include COS-7 cells, mouse L cells and CHP cells. See Sambrook (1989), supra and Ausubel et al., 1987 supplements, supra.

Various expression vectors can be used to express DNA encoding IL-10. Conventional vectors used for expression of recombinant proteins in prokaryotic or eukaryotic cells may be used. Preferred vectors include the pcD vectors described by Okayama et al., *Mol. Cell. Biol.* 3:280 (1983); and Takebe et al., *Mol. Cell. Biol.* 8:466 (1988). Other SV40-based mammalian expression vectors include those disclosed in Kaufman et al., *Mol. Cell. Biol.* 2:1304 (1982) and U.S. Pat. No. 4,675,285. These SV40-based vectors are particularly useful in COS-7 monkey cells (ATCC No. CRL 1651), as well as in other mammalian cells such as mouse L cells. See also, Pouwels et al., (1989 and supplements) *Cloning Vectors: A Laboratory Manual*, Elsevier, N.Y.

The IL-10 may be produced in soluble form, such as a secreted product of transformed or transfected yeast, insect or mammalian cells. The peptides can then be purified by standard procedures that are known in the art. For example, purification steps could include ammonium sulfate precipitation, ion exchange chromatography, gel filtration, electrophoresis, affinity chromatography, and the like. See *Methods in Enzymology Purification Principles and Practices* (Springer-Verlag, New York, 1982).

Alternatively, IL-10 may be produced in insoluble form, such as aggregates or inclusion bodies. The IL-10 in such a form is purified by standard procedures that are well known in the art. Examples of purification steps include separating the inclusion bodies from disrupted host cells by centrifugation, and then solubilizing the inclusion bodies with chaotropic agent and reducing agent so that the peptide assumes a biologically active conformation. For specifics of these procedures, see, e.g. Winkler et al., Biochemistry 25:4041 (1986), Winkler et al., Bio/Technology 3:9923 (1985); Koths et al., and U.S. Pat. No. 4,569,790.

The nucleotide sequences used to transfect the host cells can be modified using standard techniques to make IL-10 or fragments thereof with a variety of desired properties. Such modified IL-10 can vary from the naturally-occurring sequences at the primary structure level, e.g., by amino acid, insertions, substitutions, deletions and fusions. These modifications can be used in a number of combinations to produce the final modified protein chain.

The amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants. Such variants can be used in this invention as long as they retain the biological activity of IL-10.

Modifications of the sequences encoding the polypeptides may be readily accomplished by a variety of techniques, such as site-directed mutagenesis (Gillman et al., Gene 8:81 (1987)). Most modifications are evaluated by routine screening in a suitable assay for the desired characteristics. For instance, U.S. Pat. No. 5,231,012 describes a number of in vitro assays suitable for measuring IL-1 0 activity.

Preferably, human IL-10 is used for the treatment of humans, although viral IL-10 could possibly be used. Most preferably, the IL-10 used is recombinant human IL-10. The preparation of human IL-10 has been described in U.S. Pat. No. 5,231,012. The cloning and expression of viral IL-10 (BCRF1 protein) from Epstein-Barr virus has been disclosed by Moore et al, Science 248:1230 (1990).

When referring to IL-10, active fragments thereof, analogs and homologs are included. Active fragments, analogs and homologs to IL-10 include those proteins, polypeptides, or peptides which possess one or more various characteristic IL-10 activities. Examples of IL-10 activity include inhibition or substantial reduction of the level of IL-2, lymphotoxin, IL-3, or GM-CSF. IL-10 activity also includes inhibition of cytokine production by activated macrophages, e.g., IL-1, IL-6, and TNF-α.

For examples of procedures and assays to determine IL-10 activity, see U.S. Pat. No. 5,231,012. This patent also provides proteins having IL-10 activity and production of such proteins including recombinant and synthetic techniques.

Steroids suitable for use in this invention include prednisone, dexamethasone, fluticasone, betamethasone, and other steroids and derivatives thereof. In the examples which follow, the steroid used was betamethasone phosphate in a buffered saline solution. Betamethasone derivatives are commercially available from Schering Corporation, Kenilworth, N.J.

In the methods of the present invention the IL-10 is preferably combined in the same composition with the steroid. However, the combination of IL-10 plus steroid can be achieved by any means of co-administration. The co-administration can be sequential or simultaneous. "Co-administration" generally means that the multiple (two or more) therapeutics are present in the recipient during a specified time interval. Typically, if a second agent is administered within the half-life of the first agent, the two agents are considered co-administered. The invention further provides a method of predicting a mammal's predisposition for development of an inflammatory condition, characterized by suboptimal levels of IL-10, comprising assaying a sample taken from a mammal for an IL-10 level.

Suboptimal levels include undetectable amounts. A detectable level could be compared to a known normal level of IL-10. Alternatively, one can assay for inflammatory mediators such as IL-1, IL-6, TNF-a, and IFN-g by using commercially available kits. Overproduction of one of these mediators can indicate that insufficient amounts of IL-10 are available. Preferably, blood is the sample source. The method allows for prediction of predisposition to a number of inflammatory conditions, such as inflammatory bowel disease, rheumatoid arthritis, or psoriasis.

To prepare pharmaceutical compositions including IL-10 and a steroid, the IL-10 and steroid are admixed with a pharmaceutically acceptable carrier or excipient which is preferably inert. A pharmaceutical carrier can be any compatible non-toxic substance suitable for delivery of the polypeptide to a patient. Preparation of such pharmaceutical compositions is known in the art; see, e.g., *Remington's Pharmaceutical Sciences, and U.S. Pharmacopeia: National Formulary*, Mack Publishing Company, Easton, Pa. (1984).

The proportion of IL-10, steroid and additive can be varied over a broad range so long as both are present in therapeutically effective amounts. On a per-dose basis, the amount of the IL-10 will preferably range from about 0.5 to 15 µg/KG of body weight, and the amount of steroid can range from about 0.5 to 50 mg, more preferably 2 to 12 and most preferably 5 to 12 mg.

Compositions may be ingested orally or injected into the body. Formulations for oral use include compounds to protect the polypeptides from proteases which occur in the gastrointestinal tract. Injections are usually intramuscular, subcutaneous, intradermal or intravenous. Alternatively, intraarticular injection or other routes could be used in appropriate circumstances.

When administered parenterally, the compositions can be formulated in a unit dosage injectable form (solution, suspension, emulsion) in association with a pharmaceutical carrier. For instance, the IL-10 and steroid may be administered in aqueous vehicles such as water, saline or buffered vehicles with or without various additives and/or diluting agents. Examples of suitable carriers are normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. However, the IL-10 in the composition is preferably formulated in purified form substantially free of aggregates and other proteins. In addition, it should be noted that a suspension, such as a zinc suspension, can be prepared to include the polypeptide. Such a suspension can be useful for subcutaneous (SQ) or intramuscular (IM) injection.

As used herein, the phrase "therapeutically effective amount" means an amount sufficient to ameliorate a symptom or sign of a given inflammatory condition. For instance, in the case of an inflammatory condition, the signs and symptoms include one or more of pain, swelling, redness and other well known signs and symptoms of inflammation.

In the particular case of septic shock, the signs and symptoms are one or more of hypertension, microthrombi, organ failure, loss of plasma due to increased vascular permeability, as well as other known signs and symptoms of septic shock.

The term "prevention" of inflammatory conditions (such as septic shock) as used herein can be defined by the following parameters. Certain circumstances pre-dispose individuals to developing inflammatory conditions such as septic shock. For example, candidates for abdominal surgery, or any situation that would cause the rupture of or laceration of the intestines (i.e., ruptured appendix) that would entail a leakage of intestinal microflora into the abdominal cavity. Other examples include gun shot wounds, automobile accident victims with abdominal trauma, and the like. Administration of IL-10 plus at least one steroid to such individuals at high risk for developing an inflammatory condition such as septic shock prior to the onset of symptoms would ameliorate such symptoms, preventing the actual onset of the full blown manifestations of the disease.

Typical mammals that can be treated using the methods of the present invention include companion animals such as dogs and cats, and primates, including humans. Preferably, IL-10 derived from the species of the treatment target animal will be used. An effective amount for a particular patient may vary depending on factors such as the condition being treated, the overall health of the patient, the method, route, and dose of administration and the severity of side effects. Determination of the appropriate dose is made by the clinician using parameters known in the art. Generally, the dose begins with an amount somewhat less than the optimum dose and it is increased by small increments thereafter until the desired or optimum effect is achieved. (See generally *The Merck Manual §269* "Pharmacokinetics and Drug Administration.").

The preferred total daily dose of IL-10 and steroid is selected from a range of about 0.5 to 9 mg of an injectable steroid, 2.5 to 50 mg of an orally administered steroid, and 2 to 15 µg/KG of body weight of IL-10. Dosages are on a schedule which effects the desired treatment and can be periodic over short or longer term. The daily infusion rate may be varied based on monitoring of side effects, blood cell counts, and efficacy. See Gilman et al. (eds.) (1990) *Goodman and Gilman's: The Pharmacological Bases of Therapeutics* 8th ed., Pergamon Press;(1990) *Remington's Pharmaceutical Sciences,* 17th ed., Mack Publishing Co., Easton, Pa.; Avis et al. (eds.) (1993) *Pharmaceutical Dosage Forms: Parenteral Medications.* Dekker, New York; Lieberman et al. (eds.) (1990) *Pharmaceutical Dosage Forms: Tablets* Dekker, New York; and Lieberman et al. (eds.) (1990) *Pharmaceutical Dosage Forms: Disperse Systems* Dekker, New York.

Preferably, the therapeutically effective amount is a unit dose presented in an ampoule. Alternatively, the therapeutically effective amount could be presented in a vial containing multiple doses or it could be offered in some other form. The total daily dose may be given as a single injection, a continuous infusion, or it may be divided into several smaller doses for bolus intravenous administration or administration by some other route such as intramuscular injection. Compositions of the invention may also be introduced into a patient's body by an implantable or injectable drug delivery system, e.g., Urquhart et al., Ann. Rev. Pharmacol. Toxicol. 24:199 (1984); Lewis (Ed.), *Controlled Release of Pesticides and Pharmaceuticals* (Plenum Press, N.Y., 1981); U.S. Pat. No. 3,270,960; and the like.

In appropriate circumstances, multiple medications can be administered in combination. For instance, the IL-10 and steroid combination can be administered in further combination with a therapeutically effective dose of one or more additional therapeutically active agents.

The broad scope of this invention is best understood with reference to the following examples, which are not intended to limit the invention to specific embodiments.

EXAMPLES

Six mice in each group were primed with 0.5 mg heat-killed *C. parvum*, (I.V. administration) as a challenge. As a control, one group was treated with phosphate buffered saline (PBS) and Tween 20 (trademark or tradename) 0.5% one hour before challenge. As a further control, this group was treated with mouse serum albumin (MSA, a protein placebo) at the time of challenge. A second group was treated with 0.1 mg/KG betamethasone phosphate in buffered saline p.o. one hour before challenge. A third group was treated with 1 μg recombinant human IL-10 (rHuIL-10) i.p. at time of challenge. In accordance with this invention another group was treated with 0.1 mg/KG betamethasone phosphate in buffered saline p.o. one hour before challenge and 1 μg rHuIL-10 i.p. at time of challenge.

Ninety minutes after challenge blood was drawn from each mouse and tested for the concentrations TNF-α, IL-1, and IL-6. Three hours after challenge blood was drawn from each mouse and tested for IFN-γ. The results are shown in FIGS. 1 to 4.

It will be noted that in all cases the combination of IL-10 and steroid reduced the amount of inflammation-causing agent by more than either the steroid or IL-10 alone. Furthermore, in this experiment, the combined IL-10 and steroid exerted a synergistic effect in lowering the concentration of at least one inflammation-causing agent, TNF-α.

Figure 5:
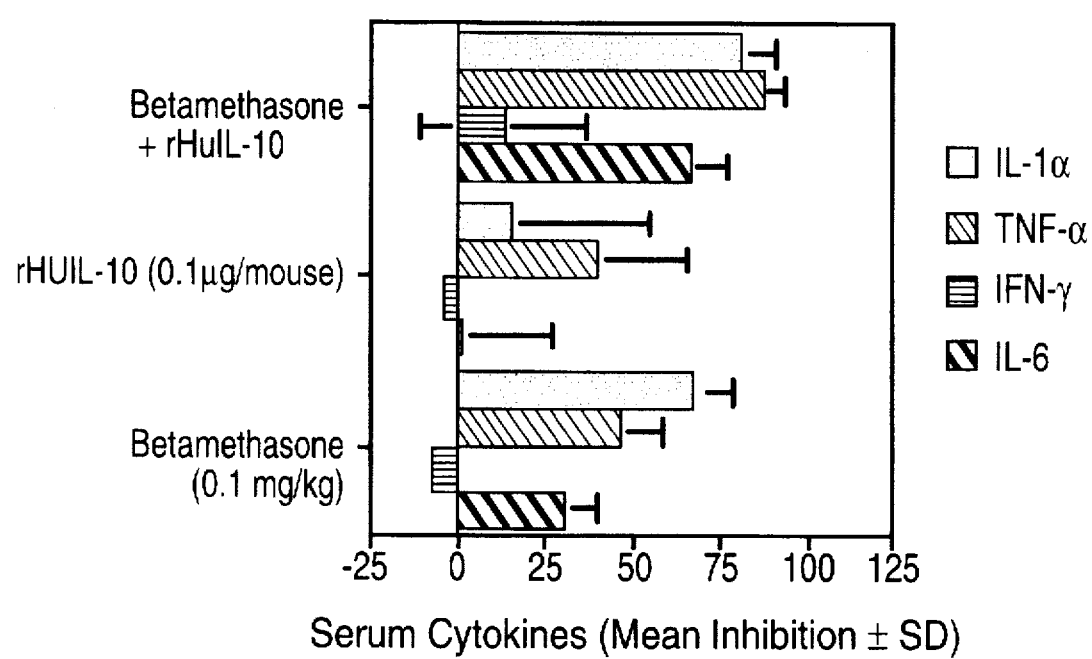
FIG. 5 illustrates the results of another experiment for mean inhibition of four serum cytokines in mice treated with betamethasone phosphate and recombinant human IL-10 in combination (the present invention), IL-10 alone, and betamethasone phosphate alone.

The results of a similar experiment are shown in FIG. 5.

Based on the above it believed that the present invention provides a method of treating or preventing inflammation, including toxic shock, that is more effective than administration of either a steroid or IL-10 alone.

Alternatively to or in addition to obtaining more effective treatment, the invention is expected to have the advantage of eliminating of reducing the well-known side effects of steroids, such as liver damage, kidney damage and increased susceptibility to infection. This advantage will result from the use of smaller amounts of steroid or a shorter course of treatment which the additive and/or synergistic combination of IL-10 and a steroid will provide.

What is claimed is:

1. A method for treating septic shock in a mammal comprising administering a therapeutically effective amount of a combination IL-10 plus at least one steroid to a mammal in need of such treatment.

2. The method of claim 1 wherein the IL-10 is human IL-10.

3. The method of claim 2 wherein the steroid is a glucocorticoid.

4. The method of claim 1 wherein the glucocorticoid is prednisone, dexamethasone, fluticasone, betamethasone, or a derivative thereof.

5. The method of claim 1 wherein the amount of IL-10 administered is from 0.5 to 15 μg/KG per day and the amount of steroid is from about 0.5 to 50 mg per day.

6. The method of claim 5 wherein the steroid is administered by injection in the amount of 0.5 to 9 mg per day.

7. The method of claim 5 wherein the steroid is administered orally in the amount of 2.5 to 50 mg per day.

8. A pharmaceutical composition comprising a combination of IL-10 plus at least one steroid.

9. The pharmaceutical composition of claim 8 wherein the IL-10 is human IL-10 and the steroid is a glucocorticoid.

10. A method for preventing septic shock in a mammal comprising administering a therapeutically effective amount of the of IL-10 plus at least one steroid to a mammal in need of such treatment .

11. The method of claim 10 wherein the IL-10 is human IL-10.

12. The method of claim 11 wherein the steroid is a glucocorticoid.

13. The method of claim 12 wherein the glucocorticoid is prednisone, dexamethasone, fluticasone, betamethosone or a derivative thereof.

14. The method of claim 10 wherein the amount of IL-10 administered is from 0.5 to 15 μg/KG per day and the amount of steroid is from 0.5 to 50 mg per day.

15. The method of claim 14 wherein the steroid is administered by injection in the amount of 0.5 to 9 mg/KG per day.

16. The method of claim 14 wherein the steroid is administered orally in the amount of 2.5 to 50 mg per day.

17. A kit for treating or preventing an inflammatory condition in a mammal comprising in combination an effective amount of IL-10 admixed with a pharmaceutical carrier and an effective amount of a steroid admixed with a pharmaceutically carrier.

18. The method of claim 4 wherein the glucocorticoid is a betamethasone.

19. The pharmaceutical composition of claim 9 wherein the glucocorticoid is a betamethasone.

20. The method of claim 13 wherein the glucocorticoid is a betamethasone.

21. The kit of claim 17 wherein the IL-10 is human IL-10.

22. The kit of claim 21 wherein the steroid is a glucocorticoid.

23. The kit of claim 22 wherein the glucocorticoid is prednisone, dexamethasone, fluticasone, betamethasone, or a derivative thereof.

24. The kit of claim 23 wherein the glucocorticoid is a betamethasone.

* * * * *